United States Patent
Albrecht et al.

(10) Patent No.: US 8,986,731 B2
(45) Date of Patent: *Mar. 24, 2015

(54) PEGYLATED LIPOSOMAL FORMULATIONS OF HYDROPHOBIC PHOTOSENSITIZERS FOR PHOTODYNAMIC THERAPY

(75) Inventors: Volker Albrecht, Jena (DE); Alfred Fahr, Cöbe/Marburg (DE); Dietrich Scheglmann, Jena-Cospeda (DE); Susanna Gräfe, Jena (DE); Wolfgang Neuberger, F.T. Labuan (MY)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 0 days.

This patent is subject to a terminal disclaimer.

(21) Appl. No.: 11/349,405

(22) Filed: Feb. 7, 2006

(65) Prior Publication Data

US 2006/0127471 A1    Jun. 15, 2006

Related U.S. Application Data

(62) Division of application No. 10/648,168, filed on Aug. 26, 2003, now abandoned.

(51) Int. Cl.
*A61K 9/127* (2006.01)
*A61K 31/407* (2006.01)
*A61K 31/555* (2006.01)
*A61K 41/00* (2006.01)

(52) U.S. Cl.
CPC ............. *A61K 9/1271* (2013.01); *A61K 31/407* (2013.01); *A61K 31/555* (2013.01); *A61K 41/0071* (2013.01)
USPC ........................................................ 424/450

(58) Field of Classification Search
USPC ........................................................ 424/450
See application file for complete search history.

(56) References Cited

U.S. PATENT DOCUMENTS

| | | | | |
|---|---|---|---|---|
| 5,000,959 A | * | 3/1991 | Iga et al. | 424/450 |
| 5,139,803 A | * | 8/1992 | Haynes et al. | 426/330.6 |
| 5,190,761 A | * | 3/1993 | Liburdy | 424/450 |

(Continued)

OTHER PUBLICATIONS

Harris and Chess, "Effect of Peguylation on Pharmaceuticals," Nature, Mar. 2003, vol. 2, pp. 214-221.

(Continued)

*Primary Examiner* — Gollamudi Kishore
(74) *Attorney, Agent, or Firm* — Bolesh J. Skutnik; BJ Associates

(57) ABSTRACT

Pharmaceutical pegylated liposomal formulations for photodynamic therapy are presented. The pegylated liposomal formulation provides therapeutically effective amounts of the photosensitizer for intravenous administration. At least one of the phospholipids in the liposomes has been linked with poly ethylene glycol (PEG) as an integral part of the phospholipids. The formed pegylated liposomes contain the hydrophobic photosensitizer within the lipid bilayer membrane. Pegylation of liposomes carrying the hydrophobic photosensitizer helps to maintain the drug level within the therapeutic window for longer time periods and provides the drug a longer circulating half life in vivo. Further the pegylated formulation of hydrophobic photosensitizers shows improved pharmacokinetics over standard non-liposomal formulations thus enhancing the efficacy of PDT with the pegylated liposomal formulations.

6 Claims, 4 Drawing Sheets

(56) References Cited

U.S. PATENT DOCUMENTS

| | | | |
|---|---|---|---|
| 5,213,804 A * | 5/1993 | Martin et al. | 424/450 |
| 5,221,796 A * | 6/1993 | Mori et al. | 554/79 |
| 5,389,378 A * | 2/1995 | Madden | 424/450 |
| 5,527,528 A * | 6/1996 | Allen et al. | 424/178.1 |
| 5,773,027 A * | 6/1998 | Bergeron et al. | 424/450 |
| 5,989,587 A * | 11/1999 | Sprott et al. | 424/450 |
| 6,017,891 A * | 1/2000 | Eibl et al. | 424/450 |
| 6,074,666 A | 6/2000 | Desai et al. | |
| 6,440,950 B1 * | 8/2002 | Zeimer | 514/63 |
| 6,498,945 B1 * | 12/2002 | Alfheim et al. | 600/407 |
| 7,354,599 B2 * | 4/2008 | Albrecht et al. | 424/450 |
| 2003/0147944 A1 * | 8/2003 | Mayer et al. | 424/450 |
| 2005/0107329 A1 | 5/2005 | Desai et al. | |

OTHER PUBLICATIONS

Mody, "Pharmaceutical development and medical applications of porphyrin-type macrocycles," Journal of Porphyrins and Phth. Vo. 4, 362-367.

Storn and Crommelin, "Liposomes: quo vadis?" PSTT, vol. 1, No. 1, Apr. 1998, 19 to 31.

* cited by examiner

Fospeg DLI 6h, 0.03 mg/kg i.v.

Fospeg DLI 6h, 0.05 mg/kg i.v.

| Before PDT | 24h post PDT | 7d post PDT | 14d post PDT | 21d post PDT | 28d post PDT |

PEGYLATED LIPOSOMAL FORMULATIONS OF HYDROPHOBIC PHOTOSENSITIZERS FOR PHOTODYNAMIC THERAPY

REFERENCE TO RELATED CASE

This application is a divisional of co-pending U.S. patent application Ser. No. 10/648,168 filed on Aug. 26, 2003 by Volker Albrecht et al., inventors, entitled "Non-polar Photosensitizer formulations for PhotoDynamic Therapy", and incorporated by reference herein.

BACKGROUND OF THE INVENTION

1. Field of the Invention

The present invention concerns the preparation of pegylated liposomal formulations containing hydrophobic photosensitizers and their use in therapy, particularly using intravenous injection.

2. Information Disclosure Statement

Liposomes are artificial vesicles composed of concentric lipid bilayers separated by water-compartments and have been extensively investigated as drug delivery vehicles. Due to their structure, chemical composition and colloidal size, all of which can be well controlled by preparation methods, liposomes exhibit several properties which may be useful in various applications. The most important properties are colloidal size, i.e. rather uniform particle size distributions in the range from 20 nm to 10 µm, and special membrane and surface characteristics. Polyethylene glycol) (PEG) are macromolecules which can be used for modification of biological macromolecules and many pharmaceutical and biotechnological applications. Liposomes can be modified by combining them with PEG.

Liposomes are used as carriers for drugs and antigens because they can serve several different purposes (Storm & Crommelin, Pharmaceutical Science & Technology Today, 1, 19-31 1998). Liposome encapsulated drugs are inaccessible to metabolizing enzymes. Conversely, body components (such as erythrocytes or tissues at the injection site) are not directly exposed to the full dose of the drug. The Duration of drug action can be prolonged by liposomes because of a slower release of the drug in the body. Liposomes possessing a direction potential, that means, targeting options change the distribution of the drug over the body. Cells use endocytosis or phagocytosis mechanism to take up liposomes into the cytosol. Furthermore liposomes can protect a drug against degradation (e.g. metabolic degradation). Although sometimes successful, liposomes have limitations. Liposomes not only deliver drugs to diseased tissue, but also rapidly enter the liver, spleen, kidneys and Reticuloendothelial Systems, and leak drugs while in circulation (Harris & Chess, Nature, March 2003, 2, 214-221).

Pegylation is an alternative method to overcome these deficiencies. First, pegylation maintains drug levels within the therapeutic window for longer time periods and provides the drug as a long-circulating moiety that gradually degrades into smaller, more active, and/or easier to clear fragments. Second, it enables long-circulating drug-containing micro particulates or large macromolecules to slowly accumulate in pathological sites with affected vasculature or receptor expression and improves or enhances drug delivery in those areas. Third, it can help to achieve a better targeting effect for those targeted drugs and drug carriers which are supposed to reach pathological areas with diminished blood flow or with a low concentration of a target antigen. The benefits of pegylation typically result in an increased stability (temperature, pH, solvent, etc.), a significantly reduced immunogenicity and antigenicity, a resistance to proteases, a maintenance of catalytic activity, and improvements in solubility, among other features, and an increased liquid stability of the product and reduced agitation-induced aggregation.

Liposome membranes containing bilayer-compatible species such as poly (ethylene glycol)-linked lipids (PEG-lipid) or gangliosides are being used to prepare stealth liposomes (Papahadjopoulos et al., PNAS, 88, 11460-4 1991). Stealth liposomes have a relatively long half-life in blood circulation and show an altered biodistribution in vivo. Vaage et al. (Int. J. of Cancer 51, 942-8, 1992) prepared stealth liposomes of doxorubicin and used them to treat recently implanted and well established growing primary mouse carcinomas, and to inhibit the development of spontaneous metastases from intra-mammary tumor implants. They concluded that long circulation time of the stealth liposomes of doxorubicin formulation accounts for its superior therapeutic effectiveness. The presence of MPEG-derivatized (pegylated) lipids in the bilayers membrane of sterically stabilized liposomes effectively furnishes a steric barrier against interactions with plasma proteins and cell surface receptors that are responsible for the rapid intravascular destabilization/rupture and RES clearance seen after i.v. administration of conventional liposomes. As a result, pegylated liposomes have a prolonged circulation half-life, and the pharmacokinetics of any encapsulated agent are altered to conform to those of the liposomal carrier rather than those of the entrapped drug (Stewart et al., J. Clin. Oncol. 16, 683-691, 1998). Because the mechanism of tumor localization of pegylated liposomes is by means of extravasation through leaky blood vessels in the tumor (Northfelt et al., J. Clin. Oncol. 16, 2445-2451, 1998; Muggia et al., J. Clin. Oncol. 15, 987-993, 1997), prolonged circulation is likely to favor accumulation in the tumor by increasing the total number of passes made by the pegylated liposomes through the tumor vasculature.

Photodynamic therapy (PDT) is one of the most promising new techniques being explored for use in a variety of medical applications and is known as a well-recognized treatment for the destruction of tumors ("Pharmaceutical development and medical applications of porphyrin-type macrocycles", T. D. Mody, J. Porphyrins Phthalocyanines, 4, 362-367 2000). Another important application of PDT is the treatment of infectious diseases due to pathogenic micro organisms including dermal, dental, suppurative, respiratory, gastro enteric, genital and other infections.

A constant problem in the treatment of infectious disease is the lack of specificity of the agents used for the treatment of disease, which results in the patient gaining a new set of maladies from the therapy.

The use of PDT for the treatment of various types of disease is limited due to the inherent features of photosensitizers. These include their high cost, extended retention in the host organism, substantial skin photo toxicity, background toxicity, low solubility in physiological solutions (which reduces its usefulness for intravascular administration as it can provoke thromboembolic accidents), and low targeting effectiveness. These disadvantages lead to the administration of extremely high doses of a photosensitizer, which dramatically increase the possibility of accumulation of the photosensitizer in non-damaged tissues and the accompanying risk of affecting non-damaged sites.

One of the prospective approaches to increase the specificity of photosensitizers and the effectiveness of PDT is a conjugation of a photosensitizer with a ligand-vector, which specifically binds to receptors on the surface of a target cell. A number of natural and synthetic molecules recognized by target cells can be used as such vectors. This approach is now used in the design of new generations of photosensitizers for the treatment of tumors ("Porphyrin-based photosensitizers for use in photodynamic therapy" E. D. Sternberg, D. Dolphin, C. Brueckner, Tetrahedron, 54, 4151-4202 1998).

Another approach to increase tumor selectivity by targeting photosensitizers to tumor cells is using liposomes, e.g. transferrin-conjugated liposomes (Derycke & De Witte, Int. J. Oncology 20, 181-187, 2002). Because non-conjugated liposomes are often easily recognized and eliminated by the reticuloendothelial system, PEG-ylated liposomes were used (Woodle & Lasic, Sterically stabilized liposomes, Biochim Biophys Acta 1113, 171-199, 1992; Dass et al., Enhanced anticancer therapy mediated by specialized liposomes. J Pharm Pharmacol 49, 972-975, 1997).

Since the application of photodynamic therapy in the treatment of cancer and other diseases is increasing rapidly, there is also a bigger demand for new photosensitizer formulations. These new pegylated photosensitizer formulations need to be stable, easy to manufacture and to handle. Furthermore, especially more hydrophobic photosensitizers, should be able to target tissue in an efficient and selective manner.

OBJECTIVES AND BRIEF SUMMARY OF THE INVENTION

It is an object of the present invention to provide an improved photosensitizer formulation for use in photodynamic therapy (PDT).

It is another object of the present invention to incorporate hydrophobic photosensitizers into a pegylated liposomal membrane.

It is yet another object of the present invention to provide a photosensitizer formulation with improved pharmacokinetic properties.

It is still another object of the present invention to improve the transport of hydrophobic photosensitizers through the cell membrane and thus increasing the efficacy of PDT.

It is also another object of the present invention to significantly reduced immunogenicity and antigenicity by pegylating the hydrophobic photosensitizer.

The present invention involves pharmaceutical pegylated liposomal formulations for photodynamic therapy. The pegylated liposomal formulation provides therapeutically effective amounts of the photosensitizer for intravenous administration. At least one of the phospholipids of the liposomes has been linked with poly ethylene glycol (PEG) as an integral part of the phospholipids. The formed pegylated liposomes contain a hydrophobic photosensitizer within the lipid bilayer membrane. Pegylation of liposomes carrying the hydrophobic photosensitizer helps to maintain the drug level within the therapeutic window for longer time periods and provides the drug a longer circulating half life in vivo. Further the pegylated formulation of hydrophobic photosensitizers shows improved pharmacokinetics thus enhancing the efficacy of PDT with the pegylated liposomal formulations.

The above, and other objects, features and advantages of the present invention will become apparent from the following description read in conjunction with the accompanying figures.

DETAILED DESCRIPTION OF PREFERRED EMBODIMENTS

Figure 1:
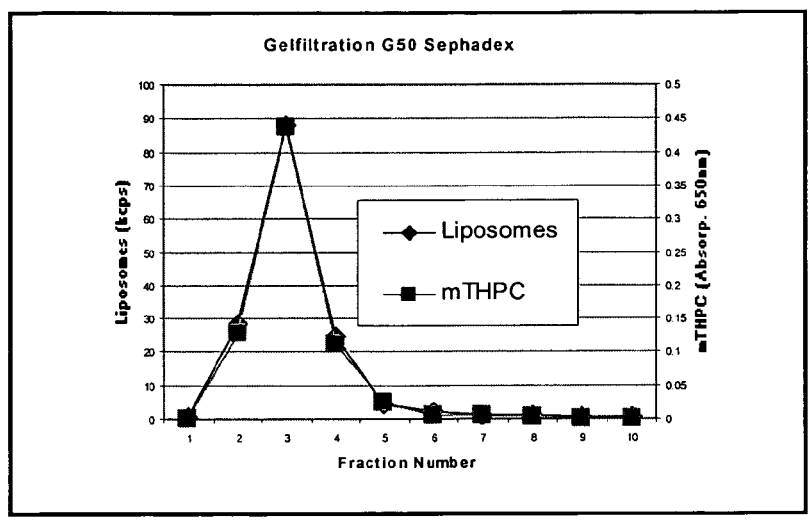
FIG. 1 is a gel filtration curve of liposomal formulated mTHPC. Both, lipid components and mTHPC show the same distribution over all fractions collected.

A pharmaceutical liposomal formulation for photodynamic therapy basically comprising a hydrophobic photosensitizer and one or more synthetic phospholipids, of which at least one has been reacted with a poly ethylene glycol, is presented. The pegylated liposomal formulation provides therapeutically effective amounts of the photosensitizer for intravenous administration. The phospholipids are modified by pegylation, i.e. they contain poly ethylene glycol (PEG) as an integral part of the phospholipids. The formed Pegylated liposomes contain the hydrophobic photosensitizer within the lipid membrane.

The hydrophobic photosensitizers in this invention include the known photosensitizers, that are advantageously employed in the practice of this invention, which includes chlorin and bacteriochlorin, and that have light absorption maxima in the range of 640-780 nanometers.

The phospholipids are modified by pegylation (containing poly ethylene glycol as integral part). The formed pegylated liposomes contain the hydrophobic photosensitizer within the membrane.

The phospholipids used in this invention preferably include DPPC (dipalmitoyl phosphatidyl choline), DPPG (dipalmitoyl phosphatidyl glycerol) and DSPE (pegylated distearoyl phosphatidyl ethanolamine), all of which are synthetically produced.

The photosensitizing formulations are useful to target the hydrophobic photosensitizer molecule to the unwanted cells or tissues or other undesirable materials and, after irradiation with an appropriated light source, to damage the target. The photosensitizing formulations are also useful to monitor unwanted cells or tissues or other undesirable materials by using fluorescence imaging methods without or with limited photochemical activation of the photosensitizer.

Especially the pegylated liposomal formulation of the invention is useful to transport hydrophobic photosensitizers. Hydrophobic substances are integrated within the membrane of the vehicles, thereby creating a structure that opens up easier, freeing the photosensitizer for action directly to the cell membrane. This mechanism delivers the photosensitizer directly to the cellular membrane system, one preferred place of action. Thus the photosensitizer, being effectively activated by illumination with an appropriate external light source, can irreversibly damage unwanted cells, tissues or other structures.

Pegylation improves tumor targeting by exploiting differences between cell types and by chemical modification of a photosensitizer conjugate. Attachment of polyethylene glycol (pegylation) to the PS increased the relative photo toxicity toward abnormal cells while reducing it towards macrophage cell lines, compared with the nonpegylated conjugate.

Conjugates were injected i.p. into adult female mice bearing tumor cells, and the pegylated conjugate gave higher amounts of photosensitizer in tumor. Taken together, these results suggest that pegylation of a polymer-photosensitizer conjugate improves tumor-targeting and may increase the efficacy of photodynamic therapy.

EXAMPLE 1

Preparation of Liposomes Containing m-THPC mTHPC (Temoporfin) was synthesized as described in U.S. Pat. Nos. 4,992,257 and 5,162,519, incorporated herein by reference.

Liposomes were prepared according to the following general procedure:

Non-polar photosensitizer and the phospholipids are dissolved in chloroform/methanol. The solution is then dried under vacuum using a rotary evaporator until the chloroform/methanol mixture is not detectable by gas chromatography anymore. Water for injection is added to rehydrate the lipid film at a temperature of 50° C. for at least 2 hours. The mixture is then passed through a homogenizer filter system using a final pore size of 100 nanometer. The filtrate is collected, filled into vials.

In one of the embodiments, liposomes are prepared from a t-butanol solution wherein the hydrophobic photosensitizer and synthetic phospholipids are dissolved in t-butanol at 50° C. This solution is then dried by evaporation at about room temperature as t-butanol crystallizes at 20° C. The powder is dispersed in water with monosaccharide and passed through a homogenizer and suitable filter. The filtrate is collected into vials.

Using the foregoing procedure, pegylated liposomal formulation were prepared as follows:

| Ingredient | Amount % w/v |
| --- | --- |
| mTHPC | 0.05 to 0.15 |
| synthetic Phosphatidyl Choline | 0.5 to 2.0 |
| synthetic Phosphatidyl Glycerol | 0.05 to 0.2 |
| pegylated Distearoyl Phosphatidyl Ethanolamine | 0.05 to 0.2 |
| Water for Injection | as required to achieve desired concentrations above |

The Phosphatidyl Choline can be one or more synthetic cholines such as dipalmitoyl phosphatidyl choline (DPPC), dimyristoyl phosphatidyl choline (DMPC), distearoyl phosphatidyl choline (DSPC). Suggested glycerols include dipalmitoyl phosphatidyl glycerol (DPPG) and dimyristoyl phosphatidyl glycerol (DMPG).

A preferred ratio of the synthetic phospholipids for phosphatidyl choline to phosphatidyl glycerol is about 10:1, see example above. Likewise a preferred range for the ratio for the phosphatidyl choline to pegylated phospholipid is about 10 to 1 to 5 to 1.

The above formulations were found to function well in their use according to the present invention. These aqueous formulation of mTHPC can be diluted with aqueous medium or biological fluids without precipitation.

In the above formulations each of the phospholipids, dipalmitoyl phosphatidyl choline and dipalmitoyl phosphatidyl glycerol, and the pegylated distearoyl phosphatidyl ethanolamine, are synthetically prepared, and are not isolatable from natural sources.

EXAMPLE 2

Physical and Chemical Stability of Pegylated Liposomal m-THPC

The physical stability of the liposomal formulations was measured by monitoring the particle size distribution by photon correlations spectroscopy.

| Stability of liposomal mTHPC | |
| --- | --- |
| Storage Conditions | Mean Particle Size distribution (nm) |
| Initial | 166 |
| 23° C. - 1 Month | 177 |
| 23° C. - 4 Month | 167 |

EXAMPLE 3

Localization of mTHPC within the Liposomal Bilayer of the Formulation

Gel filtration of liposomal formulation performed on Sephadex G50 columns. As shown in FIG. 1, lipids and mTHPC show the same distribution over all fractions indicating a physically interaction of both components i.e. integration of mTHPC into the membrane bilayer.

EXAMPLE 4

Pharmacokinetic Properties in Mice

HT 29 human colorectal carcinoma cells are used.

Six to eight weeks old adult female athymic NMRI nu/nu mice (Taconic M&B, Denmark) weighting 22-24 g were inoculated subcutaneously in the left hind thigh with 0.1 ml of $8 \times 10^7$ HT29 human colorectal carcinoma cells/ml in 5% glucose. Two to three weeks later, as the tumor reached a surface diameter of 7-8 mm, and a thickness of 2-3 mm in height, 50 µL of Temoporfin (0.2 mg/kg) diluted in ethanol or 50 µL pegylated liposomal formulation of mTHPC (0.04 mg/ml) were injected into lateral tail vein.

Following the drug injection animals were held under normal animal house lighting conditions (average illumination of 200 Lux, maximum 600 Lux of fluorescent tube light, with no exposure to sunlight or daylight). No photo-reaction was observed during this period.

Animals were sacrificed at selected time points (4, 8, 12 and 24 hrs after injection of pegylated liposomal formulated mTHPC and (8, 12, 24 and 48 hrs) after injection of Temoporfin. Four mice each were sacrificed at each mentioned time points. Immediately after the animals were killed, blood was obtained by cardiac puncture and centrifuged at 13,000×g for three minute. The resulting supernatant (blood plasma) was aspirated and stored at −70° C. for subsequent analysis. The following tissues were then dissected, weighed and also stored at −70° C.: heart, liver, lung, spleen, kidney, tumour, skin and skeletal muscle. Briefly, the plasma and tissue samples were thawed and held on ice. Accordingly, plasma was extracted as described below without further treatment. All tissue samples were cut to small pieces with a scalpel; weighed and freeze dried (Christ Freeze drying system Alpha 1-4 LSC). The resulting powdered tissue was weighed and approx. 10-20 mg was transferred to a 2.0 ml reaction tube. Accordingly 1.5 ml of methanol: DMSO (3:5, v:v) was added. The samples were immediately mixed for three-five second periods using a vortex mixer (Merck Eurolab, MELB 1719) operating at 2,400 rpm and then incubated at 60° C. with under continuous shaking for at least 12 hours. All samples were then spun at 16,000 g in a centrifuge (Microfuge, Heraeus, Germany) for five minutes. 1 ml of each supernatant was transferred to a HPLC vial and undergoing HPLC analysis.

The fluorescence wave length was set at 410 nm for excitation and 653 nm for emission. The tissue concentration of mTHPC was calculated from a calibration curve constructed by plotting the peak height values of mTHPC standard solutions versus their concentrations.

No adverse effects were seen during or immediately after injection of Temoporfin solution or pegylated liposomal formulation of mTHPC. In general, no technical differences were observed at the time between the ease of the injection of the photosensitizer in aqueous solution (Pegylated formulation) and ethanolic solution (temoporfin). A note was made of the subjective quality of each injection, since the mouse tail vein is quite small and injection was not always successful. Examination of this data shows that perfect injections were achieved in just over 87.5% of cases with Temoporfin and about 100% of cases with pegylated mTHPC. Animals in which the injection was deemed to have failed were excluded from the experiment.

Figure 2:
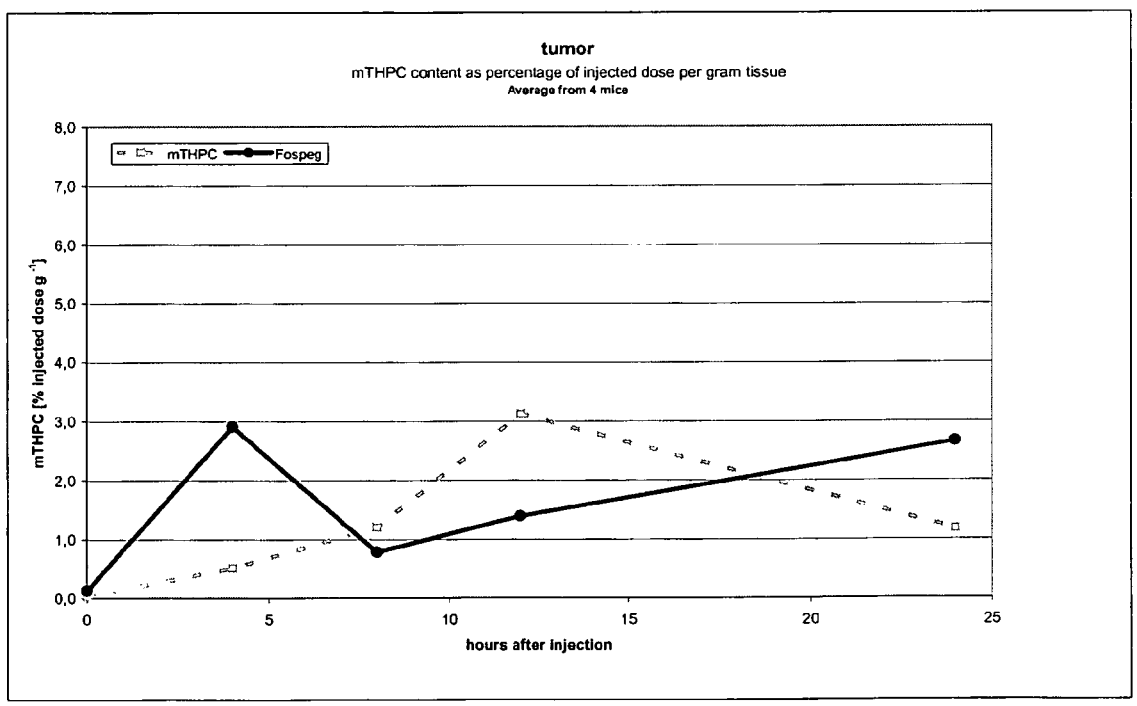
FIG. 2 shows the temoporfin content in tumor tissue for conventional and pegylated formulation of temoporfin as percentage of injected dose per gram tissue following injection of 10 µg temoporfin as solution and 2 µg pegylated liposomal formulation of temoporfin. Each time point shows the mean of four determinations.
Figure 3:
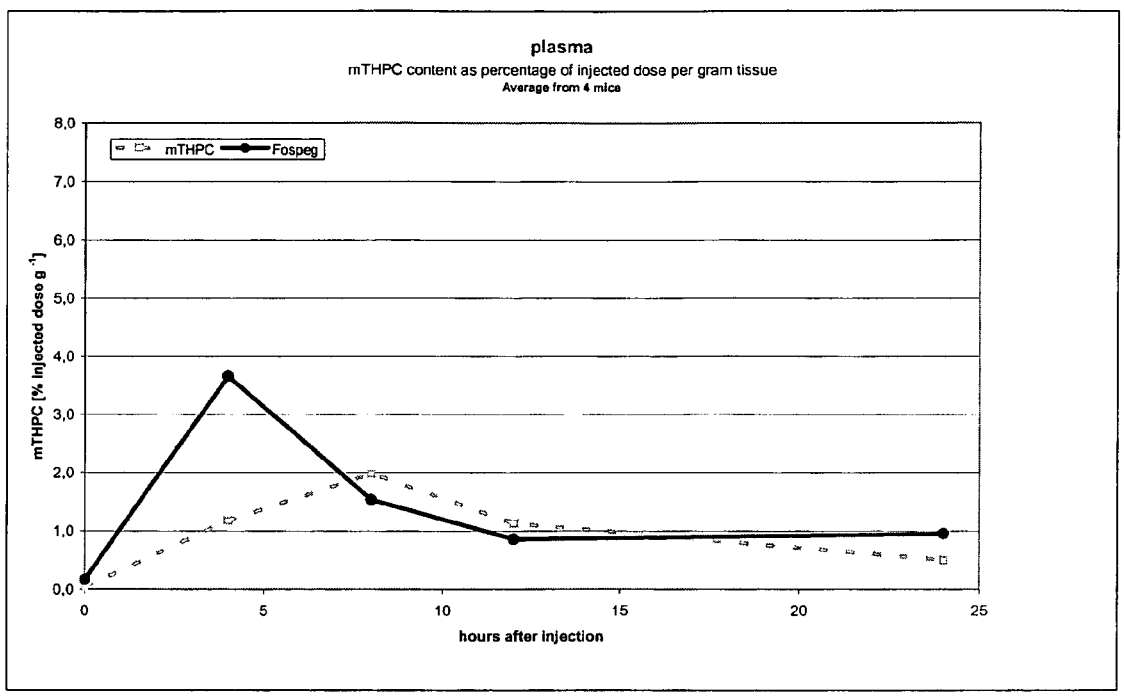
FIG. 3 illustrates the temoporfin content in plasma for convention solution and pegylated formulation of temoporfin as percentage of injected dose per gram tissue following injection of 10 µg temoporfin as solution and 2 µg pegylated liposomal formulation of temoporfin. Each time point shows the mean of four determinations.

The result of this study shows that pegylated liposomal formulation of Temoporfin shows indeed a faster pharmacokinetic than conventional temoporfin solution. FIG. 2 and FIG. 3 shows the tumor and plasma m-THPC concentration as function of time after injection of Pegylated m-THPC.

Figure 4:
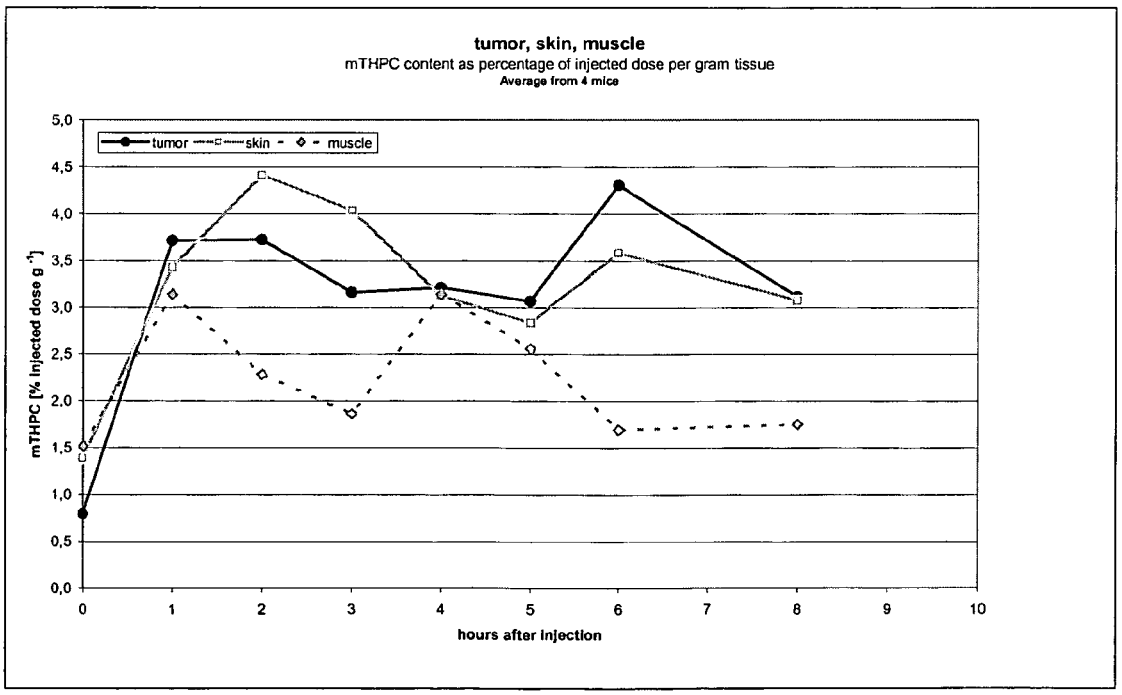
FIG. 4 shows the temoporfin content in tumor, skin and skeletal muscles as percentage of injected dose per gram tissue following injection of 2 µg pegylated liposomal formulation of temoporfin. Each time point shows the mean of four determinations.

The highest temoporfin concentration in the tumor as well as in the skin was already achieved four to eight hour after injecting pegylated formulation of temoporfin. Similarly drug concentration in skeletal muscle peaked similarly four hours after injection (FIG. 4). To summarize these results we can conclude that Photodynamic therapy in the murine model will be feasible after 4 to 8 hours post injection.

EXAMPLE 5

Pharmacokinetic Properties in Horse

Pharmacokinetic properties of aqueous formulation of m-THPC were tested in horse with equine sarcoid. Equine sarcoid is a most commonly diagnosed tumor of the skin in horses. This tumor occurs in young adult horses. It may be single or multiple, and, is mostly found on the head, the limbs and the abdomen of the horse.

Figure 6:
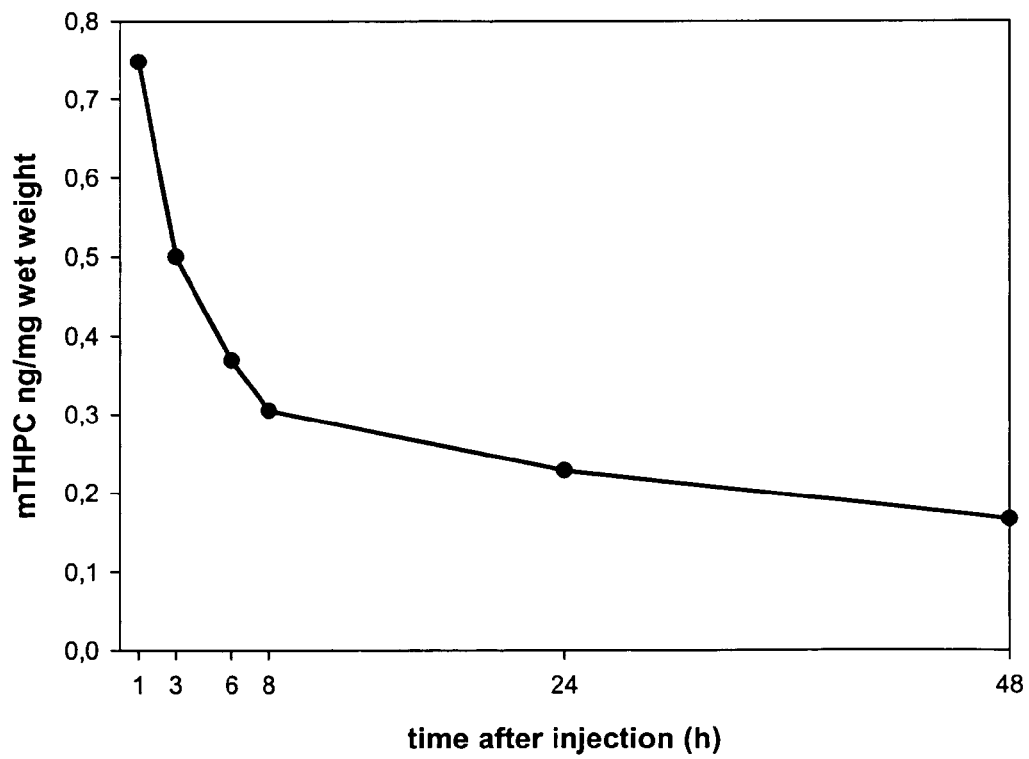
FIG. 6 shows the concentration of mTHPC in plasma of horse injected with pegylated liposomal formulation of mTHPC. Plasma samples were taken at different time and analyzed by HPCL

All the horses were injected with 0.15 mg of pegylated liposome formulation of m-THPC/kg body weight. To determine the plasma concentration of m-THPC, blood samples were obtained 5, 10, 15, 20 and 25 hours after injecting the drug. The blood samples were centrifuged and resultant supernatant (blood plasma) was aspirated and stored; and later analyzed by HPLC method (FIG. 6).

Figure 7:
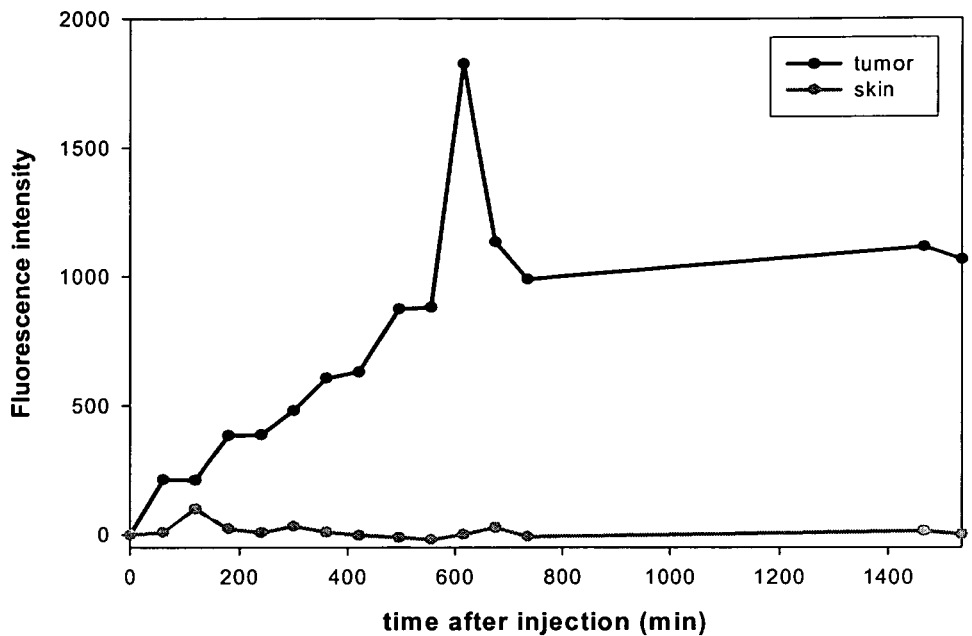
FIG. 7 shows the fluorescence measure in skin and tumor of the horse after injecting pegylated liposomal formulation of mTHPC (0.15 mg/kg) till 24 hrs.

Non-invasive fluorescence measurements have been performed at two distinct sites: tumor and skin at different times after drug administration using a optical biopsy till 24 hours after injection. Fluorescence in the tumor reached a maximum approximately 10 hrs after i.v. injection (FIG. 7). Non-invasive measurements demonstrated the trend for the better accumulation of mTHPC in the tumor compared to normal tissues.

Figure 8:
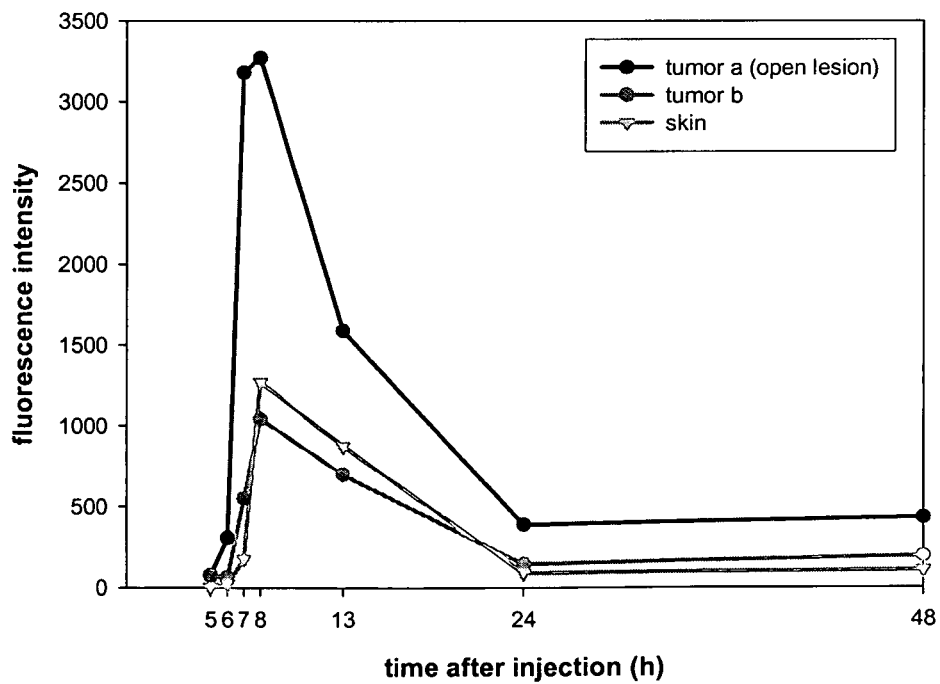
FIG. 8 shows the fluorescence measure in skin, tumors and tumors with open lesion in horse, after injecting pegylated liposomal formulation of mTHPC (0.15 mg/kg).

FIG. 8 displays the fluorescence intensity at three distinct sites: skin, tumor and tumor with open lesions as a function of time after injection of pegylated m-THPC.

EXAMPLE 6

Anti Tumor Activity of PEG Conjugated Liposomal mTHPC Formulation in Mice.

a. Drug Dose

Two different dosages 0.05, 0.03 mg/kg body weight of aqueous solution of mTHPC (in pegylated liposome) is used b. Cell Line HT29, a metastasizing human colorectal tumor cell line was used. Cells were maintained as a monolayer culture in Dulbecco's modified Eagle medium (DMEM) completed with 10% heat-inactivated fetal calf serum, 100 μg/ml streptomycin, 100 i.U./ml penicillin, at 37° C., in 95% air and 5% $CO_2$.

c. Tumor Model

Six week old athymic female mice (NMRI, nu/nu) were inoculated subcutaneously into the right hind foot with $8\times10^6$ HT29 cells. 10 days later, as the tumour had reached a diameter of approx. 10 mm; the test substance was injected intravenously. Unless indicated otherwise, 4 mice per dose and per Drug-Light-Interval (DLI) were used.

d. Photodynamic Treatment

Drug-light interval (DLI) is 6 hours. Each animal was photo irradiated at 652 nm with 10 $J/cm^2$ at 100 $mW/cm^2$ using a diode laser.

e. Evaluation of PDT Effect

Figure 5:
FIG. 5 shows correlation of drug dose in the tissue and efficacy of Photodynamic Therapy.
Figure 5:

The PDT effect of this experiment is documented by photographing the tumor at different time as shown in FIG. 5. The FIG. 5 shows the tumor pictures before PDT and after 24, hours, 1, 2, 3, 4, weeks of PDT. Mice treated to a drug dose of 0.05 mg/kg of pegylated mTHPC, a DLI of 6 h and an irradiation of 10 $J/cm^2$ a strong necrosis of the tumor tissue could be detected. The tumor was completely destroyed and 28 days after PDT no residual tumor could be detected.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A pharmaceutical liposomal formulation for photodynamic therapy, the liposomal formulation comprising:
   a liposomal bilayer, said bilayer consisting essentially of synthetic phospholipids, wherein said synthetic phospholipids are a combination of dipalmitoyl phosphatidyl choline, dipalmitoyl phosphatidyl glycerol and pegylated distearoyl phosphatidyl ethanolamine; and
   a therapeutically effective amount of temoporfin contained within said liposomal bilayer, wherein the weight ratio of the dipalmitoyl phosphatidyl choline to the dipalmitoyl phosphatidyl glycerol is 10:1;

the weight ratio of the dipalmitoyl phosphatidyl choline to the pegylated distearoyl phosphatidyl ethanolamine is from 10:1 to 5:1; and the liposomal formulation is stable for at least four months at about 23° C. without freeze-drying.

2. The liposomal formulation according to claim 1, wherein the liposomal formulation does not comprise a saccharide.

3. The liposomal formulation according to claim 1, wherein stability is determined by particle size distribution using photon correlations spectrometry.

4. The liposomal formulation according to claim 1, wherein the therapeutically effective amount of temoporfin is from 0.0001 to 0.15 percent w/v of the formulation.

5. The liposomal formulation according to claim 1, blended with an aqueous fluid for pharmaceutical administration.

6. The liposomal formulation according to claim 5, wherein pharmaceutical administration comprises intravenous injection.

* * * * *